United States Patent [19]
Nambi et al.

[11] Patent Number: 5,616,577
[45] Date of Patent: Apr. 1, 1997

[54] PROTEIN KINASE C INHIBITOR

[75] Inventors: Ponnal Nambi, Berwyn; Ashok D. Patil, King of Prussia, both of Pa.

[73] Assignee: SmithKline Beecham Corporation

[21] Appl. No.: 688,630

[22] Filed: Jul. 29, 1996

Related U.S. Application Data

[63] Continuation of Ser. No. 290,981, Aug. 25, 1994, Pat. No. 5,565,448.

[51] Int. Cl.$^6$ ................................................. A61K 31/55
[52] U.S. Cl. ............................................. 514/215; 514/824
[58] Field of Search ................................. 514/215, 824

[56] References Cited

FOREIGN PATENT DOCUMENTS

WO87/07274  12/1987  WIPO .

OTHER PUBLICATIONS

J. of Natural Products, vol. 48, No. 1, pp. 47–53 (Jan.–Feb. 1985).

J. Org. Chem., 50, pp. 4163–4164 (1985).

Experientia, 42, pp. 1064–1065 (1986).

*Primary Examiner*—Kimberly Jordan
*Attorney, Agent, or Firm*—Mary E. McCarthy; Stephen Venetianer; Edward T. Lentz

[57] ABSTRACT

The present invention relates to treatment of conditions wherein protein Kinase C inhibition is indicated.

6 Claims, No Drawings

PROTEIN KINASE C INHIBITOR

This is a continuation of application Ser. No. 08/290,981, filed Aug. 25, 1994, now U.S. Pat. No. 5,565,448.

FIELD OF THE INVENTION

The present invention relates to the treatment and prevention of conditions wherein protein kinase C (PKC) inhibition is indicated. In particular, it relates to the treatment of cardiovascular and renal disorders, inflammation, central nervous system disorders, immunosuppression, and septic shock, and to the use of certain 4,5,6,7-tetrahydropyrrolo(2,3-c)azepine-8-ones in the manufacture of medicaments for the treatment of such conditions.

BACKGROUND OF THE INVENTION

Protein kinase C is a calcium and phospholipid activated enzyme that plays a significant role in mediating the effects of a host of hormones, neurotransmitters, growth factors, antigens, and inflammatory mediators (Nishizuka, Y. (1988) *Nature,* 334:661). When these extracellular agents bind to their specific cell surface receptors, they stimulate the hydrolysis of phosphatidylinositol, phosphatidylcholine, or phosphatidylethanolamine, resulting in the accumulation of diacylglycerol which activates protein kinase C. This activation of PKC causes specific cellular substrates to be phosphorylated, resulting in the regulation of cellular processes which are closely linked to the physiological control of contractile, secretory, and proliferative processes (Nishizuka, Y. (1984) *Nature,* 308:693). As examples of physiological response induced by the system in which protein kinase C participates, there have been reported serotonin release from platelets (Kaibuchi, et al. (1982) *Cell Calcium,* 3:323; Kaibuchi, et al. (1985) *J. Biol. Chem.,* 258:6701), lysosomal enzyme release and superoxide generation from neutrophils (Kajikawa, et al. (1983) *Biochem. Biophys. Res. Commun.;* 116:743; Sehau, et al. (1983) *Biochem. Biophys. Acta,* 762:420), histamine release from mast cells (Kata Kami, et al. (1982) *Biochem. Biphys. Res. Commun.,* 121:573), secretion of aldosterone from adrenal glomerulus (Kojima, et al. (1983) *Biochem. Biophys. Res Commun.,* 116:555), and contraction of vascular smooth muscle (Rasmussen, et al. (1984) *Biochem. Biophys. Res. Commun.,* 122:776. Thus, it has been demonstrated that protein kinase C takes part in many important physiological responses in vivo. Therefore, an inhibitor of protein kinase C would be expected to be useful in the treatment of cardiovascular and renal disorders, inflammation, immunosuppression, septic shock and central nervous system disorders.

It has now been found that certain 4,5,6,7-tetrahydropyrrolo(2,3-c)azepine-8-ones previously described as alpha-adrenoceptor blocking agents and antineoplastic agents are also protein kinase C inhibitors and hence are expected to have utility in the treatment of conditions wherein protein kinase C inhibition is indicated.

SUMMARY OF THE INVENTION

The present invention provides a method of inhibiting protein Kinase C in mammals which comprises administering to the mammal in need of such treatment an effective amount of a compound of Formula (I):

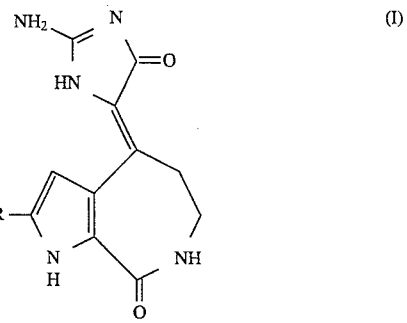

in which R is H or Br; or a pharmaceutically acceptable salt thereof.

The invention also provides for the use of a compound of Formula (I) or a pharmaceutically acceptable salt thereof in the manufacture of a medicament for the treatment of conditions wherein inhibition of protein kinase C is indicated, for example in the treatment of cardiovascular and renal disorders, inflammation, central nervous system disorders, immunosuppression, and septic shock.

DETAILED DESCRIPTION OF THE INVENTION

The present invention is a therapeutic method for treating diseases in mammals, including humans, for which inhibition of protein kinase C is indicated. The method utilizes a class of inhibitors of Formula (I).

Accordingly, the PKC inhibiting Formula (I) compounds of this invention can be used for the treatment of cardiovascular diseases, that is heart and circulatory diseases, such as thrombosis, atherosclerosis, arteriosclerosis, ischemia, reperfusion injury, and hypertension, immunosuppressive and inflammatory disorders, such as asthma, rheumatoid arthritis, psoriasis, inflammatory bowel disease, and acquired immune deficiency syndrome (AIDS), central nervous system diseases, such as stroke and trauma, septic shock based on PKC activation, and ischemia-induced renal failure. The method of this invention concerns the use of the compounds of Formula (I) as protein kinase C inhibitors in the treatment of PKC mediated disease states.

The compounds of Formula (I) can be isolated from marine sponge sources. For example, the compound wherein R is H, which is 4-(2-amino-4-oxo-2-imidazolin-5-ylidene)-4,5,6,7-tetrahydropyrrolo(2,3-c)azepine-8-one or debromohymenialdisine, has been isolated from the Great Barrier Reef sponge *Phakellia flabellata* (Sharma, et al. (1980) *J.C.S. Chem. Comm.,* 435–436) and from the Okinawan marine sponge *Hymeniaeidon aldis* (Kitagawa, et al. (1983) *Chem. Pharm. Bull.,* 31(7):2321–2328). The compound wherein R is Br, which is 4-(2-amino-4-oxo-2-imidazolin-5-ylidene)-2-bromo-4,5,6,7-tetrahydropyrrolo(2,3-c)azepine-8-one or hymenialdisine, has been isolated from the Mediterranean sponge *Axinella verrucosa* and from the Red Sea sponge *Acanthella aurantiaca* (Cimino, et al. (1982) *Tetra. Lett.,* 23(7):767–768), as well as from the Okinawan marine sponge *Hymeniaacidon aldis,* (Kitagawa, et al. (1983) *Chem. Pharm. Bull.* 31(7):2321–2328).

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, formic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The pharmaceutical carrier may be, for example, either a solid or a liquid. The administration may be parenterally, rectally, topically, transdermally or orally, the latter being the preferred route of administration. The pharmaceutical forms are, for example, syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example, polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets, granules or powder containing the active ingredient can be prepared using standard carriers and then filled into a hard gelating capsule; alternatively, a dispersion or suspension can be prepared using any suitable pharmaceutical carrier(s), for example aqueous gums, celluloses, silicates or oils and the dispersion or suspension then filled into a soft gelatin capsule.

A composition for parenteral administration which can be formulated as a solution or a suspension which will generally consist of a solution or suspension of the active ingredient in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, rectal, transdermal, or topical products.

Preferably the composition is in unit dose form. Each dosage unit for parenteral or oral administration contains perferably from 100 mg to 1000 mg of a compound of Formula (I) or a pharmaceutically acceptable salt thereof.

The daily dosage regimen for a subject in need of PKC inhibition may be, for example, an intravenous, subcutaneous, or intramuscular dose of between 100 mg and 1000 mg of a compound of Formula (I) or a pharmaceutically acceptable salt thereof, the compound being administered 1 to 4 times per day. Suitable compounds will be administered for a period of continuous therapy. Dosages for oral administration may be higher.

BIOLOGICAL DATA

Using the compounds of this invention and designated as Compound A which is 4-(2-amino-4-oxo-2-imidazolin-5-ylidene)-4,5,6,7-tetrahydropyrrolo(2,3-c)azepine-8-one or Compound B which is 4-(2-amino-4-oxo-2-imidazolin-5-ylidene)-2-bromo-4,5,6,7-tetrahydropyrrolo(2,3-c)azepine-8-one the following tests were performed:

1. In Vitro Enzyme Assays

A. Rat brain (partially purified protein kinase C)

PURIFICATION OF PROTEIN KINASE C FROM RAT BRAIN

Protein kinase C is purified from rat brain following the procedure of Walton et al. (Walton, G. H. Bertics, P. J., Hudson, L. G. Vedvick, T. S., and Gill, G. N.. *Anal. Biochem.* 161:425–437 (1987) and Woodget and Hunter (Woodget, J. R. and Hunter, T. *J. Biol. Chem.* 268:4836–4843 (1987) with the following modifications. Ammonium sulfate precipitation is performed twice (first time to 33% saturation, and the second to 70%). After centrifugation, pellets are resuspended and desalted using a G-100 column. Peak fractions are pooled, brought to 16% glycerol and 0.01% Triton X-100, and frozen in small aliquots.

SCREENING FOR PROTEIN KINASE C INHIBITORS

A high throughput screening assay utilizing 96-well microtiter plates has been developed to identify potential inhibitors of protein kinase C. The incubation volume in each well is 50 microliters containing 10 mM Tris, pH 7.5; 1.1 mM $CaCl_2$; 10 mM $MgCl_2$; 1.0 mM EGTA, 40 micrograms/ml phosphatidyl serine, 1 microgram/mL Diolein; and 100 micrograms/mL histone. The reaction is initiated by addition of 0.5 microcuries of $\gamma$-$^{32}$P-ATP (10 micromolar final concentration) subsequent to the addition of various concentrations of test compounds or extracts. The reaction is stopped after 10 minutes at 37° C. by spotting 25 microliters of the reaction mixture onto Whatman P81 paper squares using a multichannel pippettor. The squares are washed extensively in 0.5% phosphoric acid, dried with acetone, and assayed for radioactivity by liquid scintillation spectrometry. The concentrations of ATP, histone, and phosphatidyl serine used in the assay permit identification of inhibitors of both catalytic and regulatory sites of protein kinase C.

In the above enzyme assays, the $IC_{50}$ for inhibition of PKC for Compound A was about 0.5 to about 1.2 µM.

2. In Vitro Cellular and Tissue Assays

A. Inhibition of PDBu-induced contraction of rabbit aortic strip

The effect of compounds of Formula (I) in this assay is examined using the protocol in Ohlstein, et al., *J. Pharm, Exp., Ther.*, 250:548 (1989), except PDBu and compound B are substituted in place of the agonist and antagonist, respectively, therein described. Compound B showed inhibition of PDBu-induced contraction of rabbit aortic strip at an $IC_{50}$ of about 0.5 to about 0.8 µM.

B. Inhibitory Effect on in vitro TNF production by human monocytes

Assay set-up

The effects of compounds of Formula (I) on the in vitro production of TNF by human monocytes is examined using the following protocol.

Human peripheral blood monocytes are isolated and purified from either blood bank buffy coats or plateletpheresis residues, according to the procedure of Collota, R. et al., *J. Immunol.*, 132(2):936 (1984).

TNF Assay:

Immunoassay plates (96-well, Immunolon 4) are coated for 2 hours at room temperature with a murine anti-human TNFα antibody (16 μg/mL in 50 mM PBS pH 7.5). Plates are blocked with PBS containing 0.5% caesin, 0.01% thimersol, 0.001% phenol red and 0.25% Tween-20 (Block buffer) for 1 hr at 37° C. After three washings with wash buffer (consisting of PBS and 0.05% Tween-20), test samples are added to the plate and incubated overnight at 4° C. A standard titration curve is obtained by making serial dilutions of a known sample of recombinant human TNFα in block buffer identical to the test samples. Next, the plates are washed five times with wash buffer and incubated with rabbit anti-human antibody (1:1000 dilution) in block buffer for 2 hours at 37° C. Plates are washed five times with wash buffer and incubated with peroxide conjugated goat anti-rabbit antibody (1:5000 in block buffer) for 2 hours at 37° C. Following five more washes with wash buffer, substrate (o-phenylenediamine in 0.1M citrate buffer pH 4.5 containing 0.1% urea peroxide) is added to the plates for 20 min, and the color reaction is stopped by addition of 0.1M sodium fluoride. Spectroscopy (462 nM) is performed using a micro-ELISA autoreader (Titertek Multiscan MC).

C. Inhibition of glutamate-induced neurotoxicity in rat cerebellar granule cells The effect of compounds of Formula (I) in this assay is examined using the protocol in Lysko, et al, *Brain Research*, 499:258 (1989). Compound B showed inhibition of glutamate-induced neurotoxicity in rat cerebellar granule cells with an $IC_{50}$ of about 0.6 μM.

D. Inhibition of PDBu-induced serotonin release from platelets

The effect of compounds of Formula (I) in this assay is examined using the protocol in Sano, et al., *J. Biol. Chem.*, 258:2010 (1983). Compound B showed inhibition of PDBu-induced serotonin release from platelets.

E. Inhibition of PHA and ionophore-induced IL-2 production in Jurkat cells

IL-2 produced in response to PHA and ionophore in the absence or presence of compound B is assayed by an ELISA kit purchased from Advanced Magnetics, Cambridge, Mass. (Human lL-2-specific ELISA). The procedure is described by Moriya, N., *Journal of Immunoassay*, 8:131 (1987) and Robb, R., Hunam, J., *Methods in Enzymology: Immunochemical Techniques*, Section H (G.Disagato, J. Langone, and H. vanVanakis, eds.: Academic Press, N.Y., vol. 116, p. 493. 1985). Compound B showed an $IC_{50}$ of about 2 μM.

F. Inhibition of HIV syncytial assay

Chronically infected cells are employed as cell fusion centers in a rapid syncytial co-cultivation assay with uninfected CD4+ target cells. Syncytia develop overnight, in contrast to the 3 to 7 days required for the cytopathic effect to occur in similar cultures infected with cell-free virus preparations. Inhibition of fusion by soluble CD4 and other potential anti-HIV compounds is assessed using the assay described by Truneh, et al., *Cellular Immunology*, 131:98 (1990). Compound B inhibited the fusion of HIV-infected cells to CD4-positive, uninfected cells.

G. Inhibitory effect on adhesion

Assay set-up

Human umbilical cord endothelial cells were obtained from Cell Systems, (Kirkland, Wash.). Human endothelial cells were obtained as a monolayer grown in T-75 flasks. Cells were allowed to rest after shipping before being trypsinized with Trypsin/EDTA solution (1×Cell Systems Trypsin/EDTA sol). Immediately, following cell detachment, Trypsin inhibitor was added to terminate the reaction (1×Trypsin inhibitor Cell Systems) supplemented with 15% High-Clone FCS and 1% CS-HBGF consisting of αFGF and Heparin. Cells were then diluted 20-fold before being plated (250 μM) into 96-well plates that had been pre-coated with 1% gelatin (Gibco). Cells were generally used three days following passage. To ensure that human endothelial cells had formed a monolayer, plates were routinely scanned under an inverted microscope before use.

CONDITIONS FOR DETERMINING IL-8 PRODUCTION

To determine IL-8 production from human endothelial cells, the culture medium in 96-well plates was removed and replaced with 250 μl of CS-Medium (HUVEC medium), supplemented with 15% High Clone FCS. This 250 μl was removed before finally being replaced with 200 μl of HUVEC medium with high-clone serum. 25 μl of either buffer of compound B at the appropriate concentration was added to each of the 96-well plates. This was followed immediately by 25 μl of agonist at an appropriate concentration. Plates were allowed to incubate for the appropriate time in a humidified incubator at 37° C. with 5% $CO_2$. At the end of the experimental period, 150 μl of supernatant was removed from each well and transferred to a second 96-well plate. This plate was stored at 4° C. for up to 3 days without a noticeable deterioration in the quantity of IL-8 measured from the human endothelial cells. IL-8 was determined using a commercial ELISA assay (R&D Systems).

DETERMINATION OF ICAM-1 OR ELAM EXPRESSION

As for the determination of IL-8 production HUVEC were grown in 96 well plates until confluent. Each well was then treated with the appropriate concentration of compound B dissolved at 100 mM in DMSO. (Final conc of DMSO did not exceed 0.1%). Those wells which were to act as negative or positive controls also received 25 ul of buffer containing DMSO so as to give a final concentration of DMSO of 0.1%. Appropriate wells (all except the negative control) then received 25 ul of agonist (either LPS at 1000 ng/ml or TNF at between 100–250 U/ml. For ICAM the plat was allowed to incubate at 37 C 5% $CO_2$ for 6 hours while for ELAM the incubation was terminated after 4 hours. Termination was performed by washing the plate once with PBS before being fixed with 0.25% glutaraldehyde in PBS with 0.5% Gelatin (4 hours). For ICAM-1 each well was incubated with 50 ul of a 1:500 fold dilution of Monoclonal antibody 84H10 (AMAC Westbrook Me.) while for ELAM each well was incubated with the hybridoma suppernatant (50 μl/well, 1:500 fold dil) by Goat Anti-Mouse IgG & IgM Antibody-Peroxidase conjugate (Boehringer Mannheim Indianapolis Ind). Plates were washed 3×PBS+0.5% Tween 20 and developed using 1 mg/ml 0-Phenylenediamine Dihydrochloride (Sigma) in 0.05M Phosphate-citrate buffer with 0.014% $H_2O_2$ pH 5.0. Color development was determined at OD 450.

CELLULAR ADHESION ASSAY

To determine the adhesion between neutrophils and endothelial cells, human blood was obtained from laboratory personnel and the neutrophils purified by the method of Gallin et al (J. Gallin, A Rosental. (1974) J. Cell Biol. 62, pp 549–609). Neutrophils were then labeled with $^{111}$In Oxine (Medi-Physics) by incubating not more than $60\times10^6$ neutrophils with 100 μCi of $^{111}$In Oxine for 30 minutes in a volume of 1 ml. The neutrophils were then washed 3 times in PBS-$Ca^{2+}$ and $Mg^{2+}$. To determine neutrophil adhesion, endothelial cells were grown in 48 well plates by the methods described for 96 well plates except that 100 ul of the trypsinized endothelial cells were added to each well. Each well (Triplicate determinations) was treated with compound B at the appropriate concentration followed by 100 U/ml of TNF, positive and negative controls were included as appropriate. The 48 well plate was then incubated (37 C 5% $CO_2$) for 5 hours. Labeled Neutrophils ($5\times10^5$) were then placed into each well and allowed to interact with the endothelial cells for 30 minutes (at 37 C 5% $CO_2$). Each well was then gently washed 3 times with PBS to remove non-adherent cells. This was followed by adding 500 ul of 1% SDS buffer as lytic agent. The contents of each well were then transferred to polypropylene tubes before being counted for $^{111}$In content. At the same time $5\times10^5$ labeled neutrophils were placed into a polypropylene tube to determine total radioactivity incorporation.

3. In Vivo Studies:

A. Inhibition of pressor response to angiotensin II in conscious rats

Rats are prepared with indwelling femoral arterial and venous catheters and a stomach tube (Gellai, et al., *Kidney Int.* 15:419, 1979). Two to three days following surgery the rats are placed in restrainers and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously at doses of 0.1 to 300 mg/kg. The dose of compound needed to produce 50% inhibition of the control response to angiotensin II ($ED_{50}$) is used to estimate the potency of the compounds. The $ED_{50}$ of compound B is about 30 mg/kg.

B. Antihypertensive activity

The antihypertensive activity of the compounds is measured by their ability to reduce mean arterial blood pressure in conscious, spontaneously hypertensive (SHR) rats. The animals are prepared with indwelling vascular catheters are described above (A) for the administration of compounds and direct recording of blood pressure. After complete recovery from surgery (4–5 days), the rats are placed into retainers to which they have become accustomed. Mean arterial pressure is recorded continuosuly prior to and following the intravenous administration of compounds. The dose of compound needed to reduce mean arterial pressure by 25 mm Hg ($ED_{25}$) is used as an estimate of potency. The $ED_{25}$ for compound B is about 15 mg/kg.

C. Adjuvant-induced arthritis in rats

Adjuvant-induced arthritis (AA) was produced in Lewis rats by a single intradermal injection of 0.75 mg of Mycobacterium butyricum in light paraffin oil, into the base of the tail. The adjuvant arthritis occurs after a delay of approximately 10 days and is characterized by inflammation of the hindpaws. In prophylatic studies, compounds were administered daily for 5 days, beginning on the sixth day after adjuvant injection. Hindpaw volumes were measured plethysmographically on days 14, 17 and 20.

$$\% \text{ inhibition} = \frac{\text{paw volume in arthritic control rats} - \text{paw volume in drug treated rats}}{\text{paw volume in arthritic control rats} - \text{paw volume in nonarthritic rats}} \times 100$$

Daily intraperitoneal administration of compound B to AA rats produced a marked, dose related suppression of hindpaw inflammation with an $ED_{50}$ of <10 mg/kg.

D. Inhibition of tumor necrosis factor (TNF) and increased survival rate in endotoxin-treated rats The protocol used to demonstrate protection from the lethal effects of endotoxic shock is described in Badger, et al., European Patent Application Number 0 411 754, published Feb. 6, 1991 and in Hanna, Patent Cooperation Treaty Application Number WO 90/15534, published Dec. 27, 1990. In this model, Compound B inhibited the production of TNF and increased the survival rate of the animals with endotoxic shock.

What is claimed is:

1. A method of inhibiting protein kinase C in mammals which comprises administering to the mammal in need of such treatment an effective amount of a compound of formula (I):

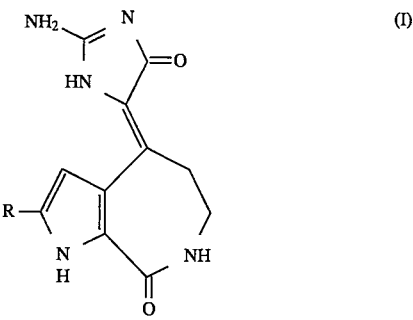

in which R is H or Br; or a pharmaceutically acceptable salt thereof.

2. The method of claim 1 wherein the compound is 4-(2-amino-4-oxo-2-imidazolin-5-ylidene)-4,5,6,7-tetrahydropyrrolo(2,3-c)azepine-8-one or a pharmaceutically acceptable salt thereof.

3. The method of claim 1 wherein the compound is 4-(2-amino-4-oxo-2-imidazolin-5-ylidene)-2-bromo-4,5,6,7-tetrahydropyrrolo(2,3-c)azepine-8-one or a pharmaceutically acceptable salt thereof.

4. The method of claim 1 for treating cardiovascular disorders.

5. The method of claim 4 for treating hypertension.

6. The method of claim 1 for treating AIDS.

* * * * *